(12) United States Patent
Zoch et al.

(10) Patent No.: US 7,608,748 B2
(45) Date of Patent: Oct. 27, 2009

(54) ABSORBENT SANITARY PRODUCT

(75) Inventors: Matthias Zoch, Heidenheim (DE); Wolfgang Ostertag, Gerstetten (DE)

(73) Assignee: Paul Hartmann AG, Heidenheim (DE)

( * ) Notice: Subject to any disclaimer, the term of this patent is extended or adjusted under 35 U.S.C. 154(b) by 79 days.

(21) Appl. No.: 10/576,088

(22) PCT Filed: Sep. 27, 2004

(86) PCT No.: PCT/EP2004/010804

§ 371 (c)(1), (2), (4) Date: Apr. 14, 2006

(87) PCT Pub. No.: WO2005/051439

PCT Pub. Date: Jun. 9, 2005

(65) Prior Publication Data

US 2007/0077841 A1    Apr. 5, 2007

(30) Foreign Application Priority Data

Nov. 29, 2003    (DE) ................................ 103 55 919

(51) Int. Cl.
*A61F 13/15* (2006.01)
*A61F 13/20* (2006.01)
(52) U.S. Cl. ....................... 604/367; 604/378
(58) Field of Classification Search .......... 604/367–378
See application file for complete search history.

(56) References Cited

U.S. PATENT DOCUMENTS

| | | | |
|---|---|---|---|
| 3,841,953 A * | 10/1974 | Lohkamp et al. ............ | 442/350 |
| 4,100,324 A * | 7/1978 | Anderson et al. ........... | 442/344 |
| 4,429,001 A | 1/1984 | Kolpin | |
| 4,531,945 A | 7/1985 | Allison | |
| 4,604,313 A | 8/1986 | Mcfarland | |
| 4,773,903 A * | 9/1988 | Weisman et al. ............ | 604/368 |
| 4,774,125 A * | 9/1988 | McAmish .................... | 428/198 |
| 4,813,948 A * | 3/1989 | Insley ......................... | 604/366 |

(Continued)

FOREIGN PATENT DOCUMENTS

EP        0 159 630        10/1985

*Primary Examiner*—Michele Kidwell
(74) *Attorney, Agent, or Firm*—Paul Vincent

(57) ABSTRACT

The invention relates to a disposable absorbent sanitary product for absorbing bodily fluids, such as diapers, incontinence pads, sanitary towels or panty liners. The product comprises a top sheet, at least sections of which are permeable to liquid, a bottom sheet, at least sections of which are liquid-tight and an absorbent body that is situated between the top sheet and the bottom sheet. According to the invention, the absorbent body comprises a first storage layer (20, 26, 30) for permanently storing bodily fluids, the layer containing 5-30 wt. % hydrophilic melt-blown microfibers (22), 70-95 wt. % particulate super-absorbent material (24) and optionally a maximum 10 wt. % particulate or fibrous component. The surface density of the melt-blown microfibers (22) is 625 g/m$^2$ and the microfibers (22) are interconnected, in a manner having strength when wet, by a plurality of melt bonds, wherein the melt-blown microfibers (22) form a dense, three-dimensional network that surrounds and immobilises the particulate super-absorbent material (24). Very few or no melt bonds are provided between the melt-blown microfibers (22) and the particulate super-absorbent material (24), such that the storage layer (20, 26, 28) has a wet-strength of at least 40% of the dry strength, as measured in the machine direction.

13 Claims, 2 Drawing Sheets

U.S. PATENT DOCUMENTS 5,591,149 A * 1/1997 Cree et al. .................. 604/378
2001/0039406 A1 * 11/2001 Hamajima et al. .......... 604/367
2003/0114066 A1 * 6/2003 Clark et al. ................. 442/361

* cited by examiner

ABSORBENT SANITARY PRODUCT

This application is the national stage of PCT/EP2004/010804 filed on Sep. 27, 2004 and also claims Paris Convention priority of DE 103 55 919.1 filed on Nov. 29, 2003.

BACKGROUND OF THE INVENTION

The present invention relates to a disposable absorbent sanitary product for absorbing body liquids, such as diapers, incontinence pads, sanitary towels or panty liners, comprising a top sheet at least sections of which are permeable to liquid, a bottom sheet at least sections of which are impermeable to liquid and an absorbent body disposed between the top sheet and the bottom sheet, the absorbent body comprising a first storage layer for permanently storing body liquids, which has hydrophilic melt-blown microfibers and particulate superabsorbing material.

Absorbent bodies with particulate superabsorbing materials and melt-blown fibers produced in a so-called "meltblown method" are known in the art. EP 0 080 382 B1 discloses e.g. a sanitary product with an absorbent body comprising, in accordance with one embodiment, 13 weight % of particulate superabsorbing material and, according to another embodiment, 17 weight % of particulate superabsorbing material, which is received and largely immobilized in a three-dimensional fiber network of melt-blown microfibers. According to the disclosure of EP 0 080 382 B1, the melt-blown microfibers preferably have a diameter of 1 to 50 µm.

EP 0 159 630 A2 discloses a sanitary product with an absorbent body comprising a first storage layer having a mixture of melt-blown microfibers, cellulose fibers and superabsorbing material. The content of superabsorbing material relative to the mass of this storage layer is between 20 and 60, preferably between 5 and 22 weight %.

WO 03/052190 A1 discloses an absorbent body structure for use in a sanitary product with thermoplastic multi-component fibers which are melt-blown microfibers, and with particulate superabsorbing material received therein. The portion of superabsorbing material is generally 5 to 90 weight %, in particular 10 to 60 weight %, and preferentially 20 to 50 weight %. The document teaches mixing of the melt-blown microfibers in the liquid molten state with the particulate superabsorbing material to form an adhesive connection between the microfibers and the particulate superabsorbing material, providing sufficient strength of the non-woven material. According to the teaching of this document, a considerable portion of cellulose fibers ("pulp fibers") of 5 to 97, preferably 35 to 95 weight % is present in addition to the thermoplastic microfibers. This document does not disclose any concrete embodiments.

WO 03/052191 A1 similarly discloses a coform non-woven material with melt-blown multi-component fibers and a second material which may also comprise or consist of superabsorbing particles. The document mentions an immense variety of ranges of the respective components for the multi-component fibers, i.e. 1 to 95 weight %, in particular 2 to 50 weight %, in particular 5 to 30 weight %, and for the particulate superabsorbing material 5 to 90, in particular 10 to 60 and preferentially 20 to 50 weight %. This document does not give any precise material compositions. It mentions that the melt-blown fibers form an adhesive connection with the second material which may comprise particulate superabsorbing material.

It is the object of the present invention to improve an absorbent sanitary product with a storage layer comprising hydrophilic melt-blown microfibers and particulate superabsorbing material such that the particulate superabsorbing material is immobilized in the dry storage layer and such that the strength of the storage layer in the wet state is increased compared to conventional products.

SUMMARY OF THE INVENTION

This object is achieved in accordance with the invention with a sanitary product having the features of the independent claim.

The present invention proposes a sanitary product with a storage layer having a very high weight % portion of particulate superabsorbing material which is received in a three-dimensional network of melt-blown microfibers. The three-dimensional network is stabilized by a plurality of melt connections among the microfibers. These are formed by whirling the microfibers during their creation, thereby forming a plurality of cross-points or intersections between the microfiber strands which melt together at these locations, at least at their surfaces. When the melt-blown microfibers are mixed with the particulate superabsorbing material, the microfibers according to the present invention have cooled or hardened to such a degree that no or hardly any adhesive connection is obtained among the microfibers and the particulate superabsorbing material, which are generally not thermally compatible. The particulate superabsorbing material is therefore substantially not adhesively bonded to the fibers of the three-dimensional network, rather mechanically enclosed. When the storage layer formed in this manner is wetted and the particulate superabsorbing material starts to swell or merges into the gel state, the three-dimensional network is not destroyed but the superabsorbing material quasi penetrates through the three-dimensional network structure with the consequence that its strength is not as impaired by wetting as in conventional absorbent body layers and absorbent body structures. The strength in the wet state of the storage layer in the machine direction is at least 40% of the strength in the dry state. Reference is thereby made to the test method discussed below.

The term microfibers as used in the present invention means fibers having a small diameter of maximally 15 µm. The microfiber diameter advantageously ranges from 1 to 15, preferably 1 to 10, and preferentially 1 to 8 µm.

To provide the fiber network formed by the melt-blown microfibers with satisfactory absorbent properties, the microfibers are made hydrophilic. This is preferably realized by adding a hydrophilic agent to the polymer forming the microfibers, which is hydrophobic per se, and preferably to the molten polymer mass. In particular, alkyl sulfonates, fatty acid derivatives or fluorine compounds have proven to be advantageous, as is described in the publication "Polymer Melt Additives: Their Chemistry, Structure and Uses" (Authors: Gasper et al. speech held at Insight 1999—Nonwoven Business/Fiber & Fabric Conferences, San Diego, Calif., 1-2 Nov. 1999, Proceedings, published by Marketing Technology Services, Inc.). A particularly advantageous hydrophilic agent is available from the company CIBA Specialty Chemicals, Basel (CH) known under the trade name Igasurf HL 560. Hydrophilic agents are advantageously used in amounts of 1 to 15%, in particular 2 to 8%, calculated as weight portion of the overall weight of the polymer.

It has proven to be particularly advantageous for the average size (average mass value) of the particulate superabsorbing material to be between 100 and 800 µm, in particular between 200 and 700 µm, determined according to the test method disclosed in EP 0 304 319 B1.

In a very important further development of the invention, the thickness of the first storage layer, measured with a test pressure of 0.5 kPa, is selected to be preferably 1.5 to 5 times, in particular 1.5 to 4 times, more preferred 1.5 to 3 times and preferentially 1.5 to 2.5 times the average size of the particulate superabsorbing materials within the storage layer. It has turned out that the inventive SAP content and fiber content provides sufficient pore volume for liquid absorption and guidance and that the SAP particles are separated from each other to such an extent that they hardly stop each other from swelling. The thickness of the first storage layer is therefore quite small considering the average particle size of between 100 and 800 µm.

In accordance with a preferred embodiment, the storage layer may have an absorption level of at least 2 cm, in particular, at least 3.5 cm in a test for vertical liquid absorption. In this connection, reference is also made to the test method discussed below.

The first storage layer may advantageously comprise one further absorbent layer on one or both sides, which comprises melt-blown microfibers in a weight % portion of at least 50, in particular at least 60, in particular at least 70, in particular at least 80 and preferentially at least 90 weight %. This absorbent layer or layers then quasi form a covering layer for the first storage layer. Their mass per unit area is preferably 2 to 10 g/m$^2$, in particular 2 to 5 g/m$^2$ i.e. relatively low. The microfiber diameter of this additional absorbent layer or additional absorbent layers is preferably smaller than the microfiber diameter of the first storage layer. A microfiber diameter for this additional absorbent layer/s of 1 to 10 µm, in particular 1 to 5 µm, preferably 1 to 3 µm has proven to be advantageous.

The microfibers of this additional absorbent layer/s are preferably also hydrophilic, in particular permanently hydrophilic.

It has also turned out to be advantageous for the microfibers of the absorbent layer/s to be thermally compatible with the microfibers of the first storage layer, in particular, formed from the same polymer.

Connecting locations between the respective fibers may be formed in this manner.

All thermoplastic polymers can be used as the polymer, in particular, polyolefines such as polypropylene and polyethylene, and also polyester such as e.g. polyethylene terephtalate.

The inventive sanitary product advantageously also has an open-pore liquid reception and distribution layer which is preferably but not necessarily formed from fibers.

Method for testing the strength in the wet and dry states:

The following test method describes a method for determining the tensile strength and the breaking elongation of absorbent bodies or absorbent body layers in the dry and wet states. The determined values permit an assessment of the adhesion between the components of the layer and provide information about their strength in the dry and wet states.

The test method is advantageously performed using a tension testing device according to EN ISO 527-1 (April 1996) and a rectangular punching knife of a size of 50 mm×150 mm (±0.25 mm).

In order to perform the test method, 5 sample bodies of a size of 50 mm×150 mm are punched out of a sheet of material, forming the sample material, in such a manner that the longer dimension is oriented parallel to the machine direction during production of the flat material sheet.

The sample piece of a size of 50 mm×150 mm is clamped on both sides on its longitudinal ends in a planar clamp whose width corresponds to at least the width of the sample, i.e. 50 mm, with a clamping length of 25 mm on both sides so that the sample length which is not clamped is 100 mm.

Since the absorbent body samples swell when liquid is added, clamping of the swelled regions into the tension testing device is problematic. The wet, swelled surface areas are squashed with the result that the sample body always breaks at the clamping location. To prevent this, the clamping location must be kept dry during swelling. This is achieved in that the respective sample body is clamped by a clamp, which practically extends over the entire width mentioned above, and is then wetted. The swelling superabsorbing material then forms a liquid-proof end within the region covered by the clamp which means that a few millimeters of the sample body in the clamped region remain dry.

The sample body clamped as described above is disposed in a bowl containing an aqueous liquid (see FIG. 6). The amount of liquid thereby depends on the amount of superabsorbing material contained in the absorbent layer. 15 g liquid per each g of superabsorbing material are conventionally used. The absorbent body sample remains in the bowl for three minutes, is then removed and initially disposed on a flat support to release the clamps. The previously clamped region of the sample body has remained dry. This dry region of the sample body is then clamped into planar clamps of the tension testing device. One end is initially clamped in the upper clamp of the tension testing device. The indicated force based on the weight of the wet sample must be adjusted to 0. The lower end of the sample body is then clamped in the lower clamp without tension. It is clamped such that the transition region between the dry longitudinal end of the sample body and the wetted region of the sample body is located outside of the clamped zone.

The test involves at least n=5 individual measurements for each sample body. The clamps of the tension testing device are then moved apart with a testing speed of 100 mm/min and the resulting tensile force within the sample body in the direction of the test motion is determined. The force under which the sample body breaks is called the breaking strength and defines the measured strengths of a dry sample body and of a body wetted in the above-described manner.

Vertical Liquid Absorption:

This test method measures the wick effect of a sample body, i.e. its capacity of absorbing liquid and actively distributing it, i.e. without the assistance of gravity etc.

The required test devices are a water container, a sample holder with a stand, precision scales, a punching knife for punching the sample body out of a flat sheet material in the machine direction, a stop watch and a test solution which is a 0.9% solution of NaCl in demineralized water. Sample bodies of dimensions of 100 mm×150 mm (0.25 mm) are punched out of a flat sheet material using the punching knife. The sample body formed in this manner is clamped with one free longitudinal end on the sample holder and is freely suspended into the initially empty water container. The test solution is then carefully filled into the water container such that the lower free end of the sample body is immersed into the liquid. After 20 minutes, the level to which the liquid has risen in the sample body, which is due to capillary suction effect in the sample body, is determined and recorded in centimeters.

Further features, details and advantages of the invention can be extracted from the claims, the drawing and the following description of the inventive sanitary product.

DESCRIPTION OF THE PREFERRED EMBODIMENT

Figure 1:
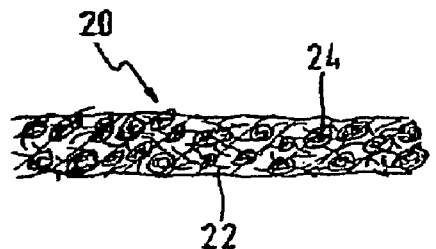
FIG. 1 shows a schematic section view of a storage layer of an inventive sanitary product.

FIG. 1 shows a section view of an inventive storage layer 20. The storage layer 20 comprises hydrophilic polypropylene melt-blown fibers 22 with a fiber diameter of 3 to 6 μm. The mass per unit area of the fiber portion is 20 g/m². The storage layer 20 moreover comprises SAP particles 24 having an average particle size (average mass value) of approximately 400 μm. The mass per unit area of the SAP particles 24 is 220 g/m². The weight-related SAP portion is therefore 91.5%. The thickness of the storage layer is 1.2 mm.

The absorption level of the storage layer 20 is 3.5 cm, as measured in the test method described above. The tensile strength in the dry state of this storage layer 20 was 6.1 N, according to the test method described above. The tensile strength in the wet state was 3.6 N, according to the test method described above.

Figure 2:
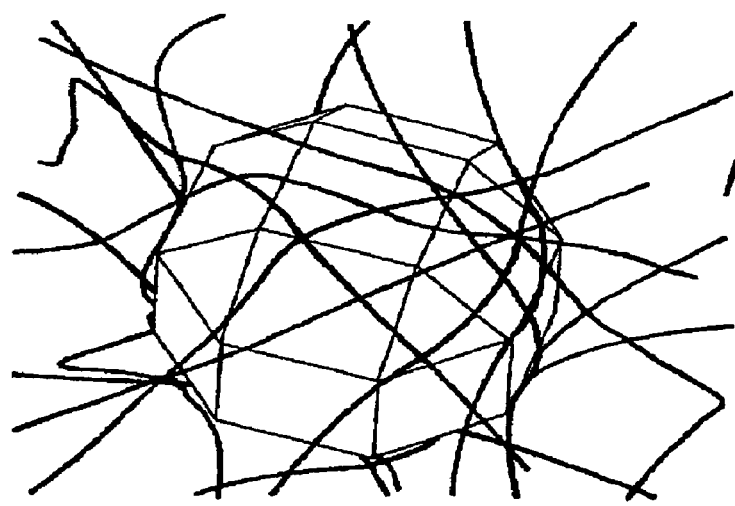
FIG. 2 is a sketch, taken to scale, showing embedding of a particle of superabsorbing material in a three-dimensional network structure of microfibers.

FIG. 2 shows an enlarged but properly scaled schematic illustration of an SAP particle 24 having an actual size of 450 μm, which is embedded in a three-dimensional network of melt-blown fibers 22.

Figure 3:
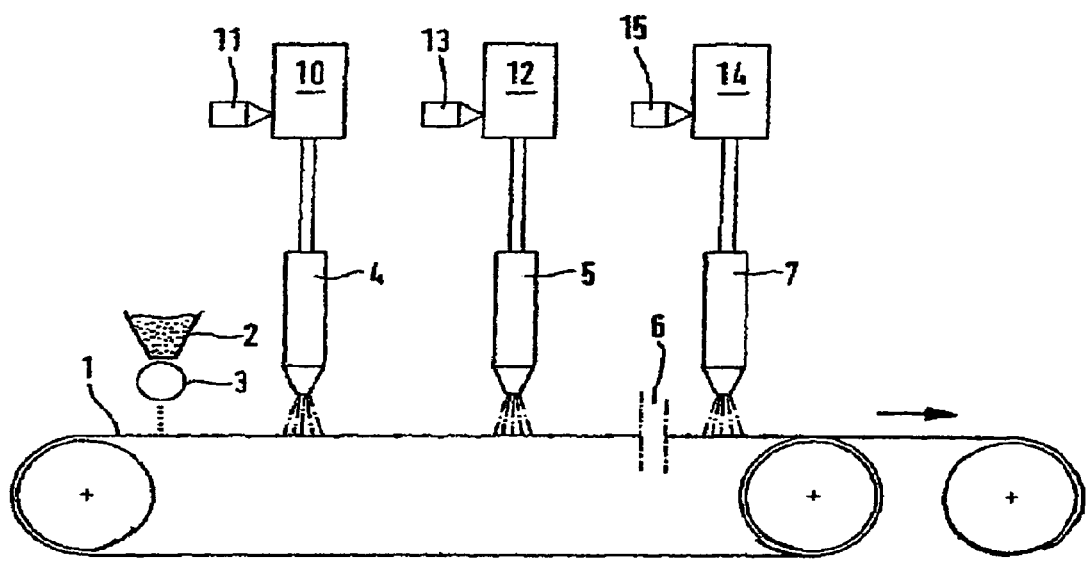
FIG. 3 is a schematic view of a fiber composite material production system.
Figure 6:
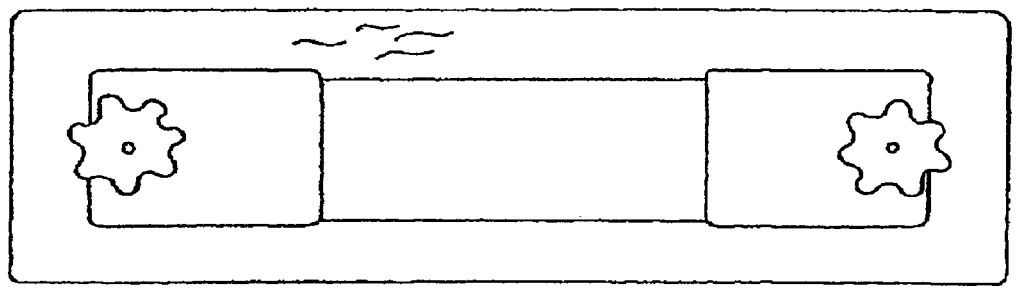
FIG. 6 shows a clamped sample body during wetting.

The storage layer 20 is produced using a fiber composite material production system shown in FIG. 3. The SAP particles were dosed, via the solid matter feeding means 2 and the distributing roller 3, onto a belt 1 of Teflon continuously moving in the direction of the arrow. An air flow containing the melt-blown fibers was directed onto this SAP particle layer via a melt-blown fiber forming unit comprising a melt-blown polymer dosing device 10, a dosing device 11 for additives such as hydrophilic agents and a melt-blown nozzle device 4, in such a manner that the SAP particles and the melt-blown fibers on the belt were whirled and therefore not layered but largely homogeneously mixed. The temperature and speed of the air flow containing the melt-blown fibers were selected such that only a small part of the SAP particles and the melt-blown fibers melted together. The other melt-blown fiber forming units (5, 12, 13 and 6, 7, 14, 15) were deactivated.

It is clear that the SAP particles and the melt-blown fibers can be mixed in a different manner as described above, e.g. by directly dosing the SAP particles into the air flow containing the melt-blown fibers, wherein the fiber/SAP mixture thereby obtained is subsequently disposed on the belt for forming the inventive storage layer, as is disclosed e.g. in the above-cited documents EP 0 159 630 A2 or WO03/052190. The extent and number of melt connections between SAP particles and melt-blown fibers can be selectively influenced, in particular, by controlling the temperature of the air flow containing the melt-blown fibers before and after adding the SAP particles. The lower the temperature of the melt-blown fibers when they contact the SAP particles, the less they melt with the SAP particles, while the melt connections among the fibers, i.e. within thermally compatible materials, are formed at even low temperatures. This applies of course only if the melt-blown fibers have not completely cooled and hardened but still have a certain residual adhesion ("tackiness").

In a further inventive embodiment according to FIG. 1, the storage layer comprises hydrophilic polypropylene melt-blown fibers with a fiber diameter of 3 to 6 μm. The mass per unit area of the fiber portion is 13 g/m². The storage layer also comprises SAP particles having an average particle size of approximately 350 μm. The mass per unit area of the SAP particles is 220 g/m². The weight-related SAP portion is therefore 93.60%. The thickness of the storage layer is 1.0 mm.

Figure 4:
FIG. 4 shows a section view of an absorbent body layer comprising a top layer.

FIG. 4 shows a section view of an advantageous further development of a two layer absorbent body 26. The two layer absorbent body 26 has a preferably SAP-free, melt-blown fiber layer 28 on one side as a further absorbent layer. The diameter of the fibers of this layer is 2 to 3 μm. The mass per unit area is only 4 g/m². Towards this end, a thin melt-blown fiber layer is directly disposed on the above-described inventive storage layer using a further downstream melt-blown fiber forming unit (5, 12, 13) such that this melt-blown fiber layer and the absorbent body layer form an adhesive bond. The third melt-blown fiber forming unit (6, 7, 14, 16) shown in FIG. 3 is deactivated.

Figure 5:
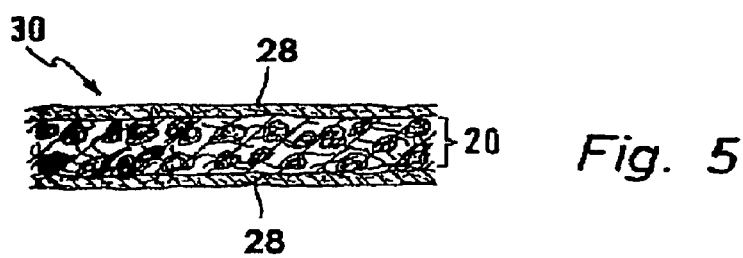
FIG. 5 shows a section view of an absorbent body layer with top sheets on both sides.

FIG. 5 shows a further advantageous development of a three layer absorbent body 30 The three layer absorbent body 30 has absorbent layers on both sides, in particular SAP-free melt-blown fiber layers 28. This further development of the absorbent body layer can be produced by disposing a first thin melt-blown fiber layer directly on the first surface of the above-described inventive storage layer 20 using a subsequent further melt-blown fiber forming unit (5, 12, 13) as described above. This layer compound is subsequently turned using conventional methods (reference numeral 6) and then a second thin layer of melt-blown fibers is directly disposed in an analogous fashion on the second surface of the storage layer, using a subsequent further melt-blown fiber forming unit (7, 14, 15).

The inventive storage layers which are coated with melt-blown fibers on one or both sides advantageously improve the liquid distributing capacity and the strength in the wet and dry states and also effectively prevent the SAP particles from escaping the storage layer.

We claim:

1. A disposable sanitary product, a diaper, an incontinence pad, a sanitary towel, or a panty liner for absorbing body liquids, the product comprising:

a top sheet at least sections of which are permeable to liquid;

a bottom sheet at least sections of which are impermeable to liquid; and an absorbent body disposed between said top sheet and said bottom sheet, said absorbent body comprising a storage layer for permanently storing body liquids, the storage layer having 5 to 30 weight % of hydrophilic melt-blown microfibers and 70 to 95 weight % of particulate superabsorbing material, wherein a mass per unit area of said melt-blown microfibers is 6 to 25 g/m², said melt-blown microfibers being connected to each other by a plurality of melt connections to ensure stability in a wet state in such a manner that said melt-blown microfibers form a dense, three-dimensional network which surrounds and immobilizes said particulate superabsorbing material, wherein substantially no melt connections are provided between said melt-blown microfibers and said particulate superabsorbing material, said storage layer having a strength in a wet state, measured in a machine direction, of at least 40% of a strength thereof in a dry state.

2. The sanitary product of claim 1, wherein said storage layer further comprises up to 10 weight % of a further particulate or fibrous component.

3. The sanitary product of claim 1, wherein an average size of said particulate superabsorbing material $D_{SAP}$ is 100 to 800 μm and a thickness of said storage layer $D_{1sp}$ is between $D_{SAP}$ * 1.5 and $D_{SAP}$ * 5, between $D_{SAP}$ * 1.5 and $D_{SAP}$ * 4, between $D_{SAP}$ * 1.5 and $D_{SAP}$ *3, or between $D_{SAP}$ * 1.5 and $D_{SAP}$ * 2.5.

4. The sanitary product of claim 1, wherein an absorption level of said storage layer is at least 2 cm, at least 3 cm, at least 4 cm, at least 5 cm, or at least 6 cm.

5. The sanitary product of claim 1, wherein said storage layer has a bottom absorbent layer facing said bottom sheet, said bottom absorbent layer having melt-blown microfibers of an amount of 100 to 50 weight %, 100 to 60 weight %, 100 to 70 weight %, 100 to 80 weight %, or of 100 to 90 weight %.

6. A disposable sanitary product, a diaper, an incontinence pad, a sanitary towel, or a panty liner for absorbing body liquids, the product comprising:
   a top sheet at least sections of which are permeable to liquid;
   a bottom sheet at least sections of which are impermeable to liquid; and
   an absorbent body disposed between said top sheet and said bottom sheet, said absorbent body comprising a storage layer for permanently storing body liquids, the storage layer having 5 to 30 weight % of hydrophilic melt-blown microfibers and 70 to 95 weight % of particulate superabsorbing material, wherein a mass per unit area of said melt-blown microfibers is 6 to 25 $g/m^2$, said melt-blown microfibers being connected to each other by a plurality of melt connections to ensure stability in a wet state in such a manner that said melt-blown microfibers form a dense, three-dimensional network which surrounds and immobilizes said particulate superabsorbing material, wherein substantially no melt connections are provided between said melt-blown microfibers and said particulate superabsorbing material, said storage layer having a strength in a wet state, measured in a machine direction, of at least 40% of a strength thereof in a dry state, wherein said storage layer has a top absorbent layer facing said top sheet, said top absorbent layer having melt-blown microfibers in an amount of 100 to 50 weight %, 100 to 60 weight %, 100 to 70 weight %, 100 to 80 weight %, or 100 to 90 weight %.

7. The sanitary product of claim 5, wherein a mass per unit area of said bottom absorbent layer is 2 to 10 $g/m^2$ or 2 to 5 $g/m^2$ and a fiber diameter of said melt-blown microfibers of said bottom absorbent layer is smaller than a fiber diameter of said melt-blown microfibers of said storage layer.

8. A disposable sanitary product, a diaper, an incontinence pad, a sanitary towel, or a panty liner for absorbing body liquids, the product comprising;
   a top sheet at least sections of which are permeable to liquid;
   a bottom sheet at least sections of which are impermeable to liquid; and
   an absorbent body disposed between said top sheet and said bottom sheet, said absorbent body comprising a storage layer for permanently storing body liquids, the storage layer having 5 to 30 weight % of hydrophilic melt-blown microfibers and 70 to 95 weight % of particulate superabsorbing material, wherein a mass per unit area of said melt-blown microfibers is 6 to 25 $g/m^2$, said melt-blown microfibers being connected to each other by a plurality of melt connections to ensure stability in a wet state in such a manner that said melt-blown microfibers form a dense, three-dimensional network which surrounds and immobilizes said particulate superabsorbing material, wherein substantially no melt connections are provided between said melt-blown microfibers and said particulate superabsorbing material, said storage layer having a strength in a wet state, measured in a machine direction, of at least 40% of a strength thereof in a dry state, wherein said storage layer has a top absorbent layer facing said top sheet, said top absorbent layer having melt-blown microfibers in an amount of 100 to 50 weight %, 100 to 60 weight %, 100 to 70 weight %, 100 to 80 weight %, or 100 to 90 weight %, wherein a mass per unit area of said top absorbent layer is 2 to 10 $g/m^2$ or 2 to 5 $g/m^2$ and a fiber diameter of said melt-blown microfibers of said top absorbent layer is smaller than a fiber diameter of said melt-blown microfibers of said storage layer.

9. The sanitary product of claim 5, wherein said melt-blown microfibers of said bottom absorbent layer are thermally compatible with said melt-blown microfibers of said storage layer.

10. The sanitary product of claim 6, wherein said melt-blown microfibers of said top absorbent layer are thermally compatible with said melt-blown microfibers of said storage layer.

11. The sanitary product of claim 1, further comprising a porous or fibrous layer disposed between said storage layer and said top sheet to rapidly absorb liquid.

12. The sanitary product of claim 1, wherein a strength in a wet state is at least 50%, at least 60%, at least 70%, at least 80%, or at least 90% of a strength in a dry state.

13. The sanitary product of claim 1, wherein said storage layer consists essentially of melt-blown microfibers and particulate superabsorbing material.

* * * * *